(12) United States Patent
Edmonson et al.

(10) Patent No.: US 7,608,978 B2
(45) Date of Patent: Oct. 27, 2009

(54) SENSING SYSTEMS UTILIZING ACOUSTIC WAVE DEVICES (76) Inventors: Peter J. Edmonson, 138 Stone Church Road East, Hamilton, Ontario (CA) L9B 1A9; William D. Hunt, 109 Kirk Crossing Dr., Decatur, GA (US) 30030

( * ) Notice: Subject to any disclaimer, the term of this patent is extended or adjusted under 35 U.S.C. 154(b) by 0 days.

(21) Appl. No.: 11/812,687

(22) Filed: Jun. 21, 2007

(65) Prior Publication Data

US 2008/0315718 A1 Dec. 25, 2008

(51) Int. Cl.
*H03H 9/58* (2006.01)
*H03H 9/64* (2006.01)
(52) U.S. Cl. .................... 310/313 R; 331/158; 333/189
(58) Field of Classification Search ................. 310/336, 310/332.21
See application file for complete search history.

(56) References Cited

U.S. PATENT DOCUMENTS

| | | | | |
|---|---|---|---|---|
| 4,361,026 A | * | 11/1982 | Muller et al. | ............. 73/24.01 |
| 5,189,914 A | * | 3/1993 | White et al. | .................. 73/599 |
| 6,626,026 B2 | * | 9/2003 | Banda et al. | ............... 73/24.01 |
| 7,053,524 B2 | * | 5/2006 | Edmonson et al. | ...... 310/313 D |
| 7,229,821 B1 | * | 6/2007 | Edmonson et al. | ....... 435/287.1 |

OTHER PUBLICATIONS

Campell, C.K. et al, Study of a UHF Mobile Radio Receiver Using a Voltage-Controlled SAW Locak Oscillator; Jan. 1984 IEEE Transactions on Sonics and Ultrasonics, vol. SU-31, No. 1.

Saw, C.B, et al, Multifrequency Pulsed Injection-Locked Oscillator Using a Novel Low-Loss Saw Comb Filter; 1986 Ultrasonics Symposium, IEEE.

* cited by examiner

*Primary Examiner*—Jaydi SanMartin
(74) *Attorney, Agent, or Firm*—Steven M. Greenberg, Esq.; Carey, Rodriguez, Greenberg & Paul, LLP (57) ABSTRACT

A sensing system includes an acoustic wave device comprising a body of piezoelectric material, and a first electrode assembly mounted on the piezoelectric body whereby an appropriate input applied to the electrode assembly produces an acoustic wave in the piezoelectric body and a first frequency response. The acoustic wave device also has a second electrode assembly to produce a second frequency response, the second electrode assembly being in contact with an area sensitive to a supplied stimulus to cause a characteristic of the sensitive area to change when a supplied stimulus is sensed to thereby change the second frequency response. The acoustic wave device has an output connected to the input of an amplifier, the amplifier having an output connected to the input of a coupling device. The coupling device is connected to the input of the acoustic wave device and has an output connected to a detector. The acoustic wave device, the amplifier and the coupling device are configured to be in an "off" condition when no supplied stimulus is sensed by the sensitive area of the acoustic wave device and to be in an "on" condition when a supplied stimulus is sensed by the sensitive area. The coupling device is configured to send a change signal to the detector when a change from the "off" condition to the "on" condition occurs.

18 Claims, 9 Drawing Sheets

SENSING SYSTEMS UTILIZING ACOUSTIC WAVE DEVICES

FIELD OF INVENTION

This invention relates to sensing systems utilizing acoustic wave devices.

BACKGROUND OF THE INVENTION

Sensing systems utilizing acoustic wave devices are known and have been proposed for sensing various stimuli, such as biological material and explosive material. However, a need exists for an improved sensing system of this kind.

SUMMARY OF THE INVENTION

The present invention provides a sensing system in which an acoustic wave device is utilized in an improved manner, with the operation of the system being similar to that of an injection-locked oscillator which, in turn, has a circuit which is equivalent to a neural network. In its simplest form, the present invention permits the construction of a functional switch utilizing a single acoustic wave device configured as an injection-type oscillator. The present invention can also provide a functional equivalent of a logic AND gate by utilizing two or more acoustic wave devices configured as injection-type oscillators.

A major use of such a sensing system may be as a low cost test platform which can be purchased commercially and which has a low probability of false positives and false negatives for a particular test. A simple pregnancy test is a known example of a commercial product which tests for only one indicator, with the result that there is some uncertainty in the test results. Another known example is the PSA or prostate specific antigen test which again tests for only one indicator.

The present invention can provide a low cost, commercially available product which can be used to test several indicators relating to a specific concern, such that all indicators would have to be present in adequate amounts before a positive indication would result. A further use of this invention would be the mapping of a biological signalling and pathway network onto the system itself. In this case, the induced frequency shift of an acoustic wave device would be due to the presence of biomarkers, which participate in a cascade of molecular events in a cell or a group of cells. Other sensing systems in accordance with the present invention can be implemented where the intelligence is inherent to injection-type oscillators performing together as a neural network.

This present invention eliminates the need for a complicated and costly microprocessor, application-specific integrated circuitry (ASIC) and associated data acquisition circuitry to evaluate the sensed input stimuli. A sensing system in accordance with the present invention may comprise an acoustic wave device, an amplifier, a simple alert circuit and an energy source. A more complicated system which will function as a multiple AND gate will require multiple acoustic wave devices, multiple amplifiers, a simple alert circuit and an energy source.

The present invention is well suited to provide a low cost commercial type of test platform in which a consumer could purchase the system, take it home or to any other convenient place and perform a test with sufficient vapor or fluid. One example would be a preliminary home Asthma test where the consumer would provide the sensing system with a vapor sample and the acoustic wave device would detect selected biomarkers associated with Asthma. All of the selected biomarkers would have to be present and of sufficient quantities to produce a positive reading. Examples of such biomarkers for Asthma have been published by K. Matsunaga et al, "Airway cytokine expression measured by means of protein array in exhaled breath condensate: Correlation with physiologic properties in asthmatic patients." Journal of Allergy and Clinical Immunology, Volume 118, Issue 1, Pages 84-90, 2006. The present invention can be applied to many other examples of low cost commercial types of platform, for example testing for allergies such as mold, various types of Cancer and other health related diseases. The present invention is also well suited for the testing of many of the signaling molecules referred to in D. Stubbs, W. D. Hunt and P. J. Edmonson, "SURFACE ACOUSTIC WAVE IMMUNOSENSORS FOR THE DETECTION OF SIGNALING MOLECULES IN A BIOLOGICAL ENVIRONMENT", U.S. patent application Ser. No. 11/226,261, filed Sep. 15, 2005.

This invention can be used for the identification of potential health related illnesses utilizing logic functions and multiple biomarkers. Tests which involve logic rules and functions from the combination of various biomarkers have the potential to improve diagnostic performance over single markers, as outlined by R. Etzioni et al, "Combining biomarkers to detect disease with application to prostate cancer," Biostatistics, 4, 4, pp. 523-538, Oxford University Press, 2003.

The present invention thus provides a sensing system including a detector and an oscillating circuit comprising a coupling device, an amplifier, and a plurality of resonators. Each resonator comprises (i) a body of piezoelectric material, (ii) an input electrode assembly mounted on the body of piezoelectric material whereby the input electrode assembly when activated produces an acoustic wave across the body of piezoelectric material, and (iii) an output electrode assembly mounted on the body of piezoelectric material and being in contact with a sensitive area that is sensitive to a supplied stimulus so that the acoustic velocity of the acoustic wave across the sensitive area is modified when a supplied stimulus binds to the sensitive area in sufficient quantity, whereby the output electrode assembly receives the acoustic wave after the acoustic wave has passed across the sensitive area. For each resonator, when the input electrode assembly is activated, the input electrode assembly and the output electrode assembly cooperate to produce a frequency response representative of one of presence or absence of a sufficient Quantity of the stimulus. The resonators are coupled in series from 1 to n, and the $n^{th}$ resonator has an output connected to an amplifier input of the amplifier, the amplifier has an amplifier output connected to a coupling device input of the coupling device, the coupling device has a first coupling device output connected to the input of the first resonator and a second coupling device output connected to the detector. The amplifier has a gain that is insufficient to cause the oscillator circuit to meet Barkhausen criteria when at least one of the n resonators produces a frequency response representative of absence of a sufficient quantity of its respective stimulus, and which gain is sufficient to cause the oscillator circuit to meet Barkhausen criteria when all of the n resonators produce a frequency response representative of presence of a sufficient quantity of their respective stimulus. Thus, the detector emits a detection signal only when all of the n resonators produce a frequency response representative of presence of a sufficient quantity of their respective stimulus.

The electrode assembly and the piezoelectric body may form a resonator which resonates at said first frequency and the second electrode assembly and the piezoelectric body form a resonator which resonates at said second frequency.

The acoustic wave device may comprise a plurality of sensitive areas on the same or separate piezoelectric-bodies, each sensitive area at being sensitive to a different stimulus whereby the "on" condition occurs only when every sensitive area senses the stimulus to which it is sensitive.

The at least one sensitive area may comprise molecular recognition elements or antibodies.

BRIEF DESCRIPTION OF THE DRAWINGS

Embodiments of the invention will now be described, by way of example, with reference to the accompanying drawings, of which.

Figure 1:
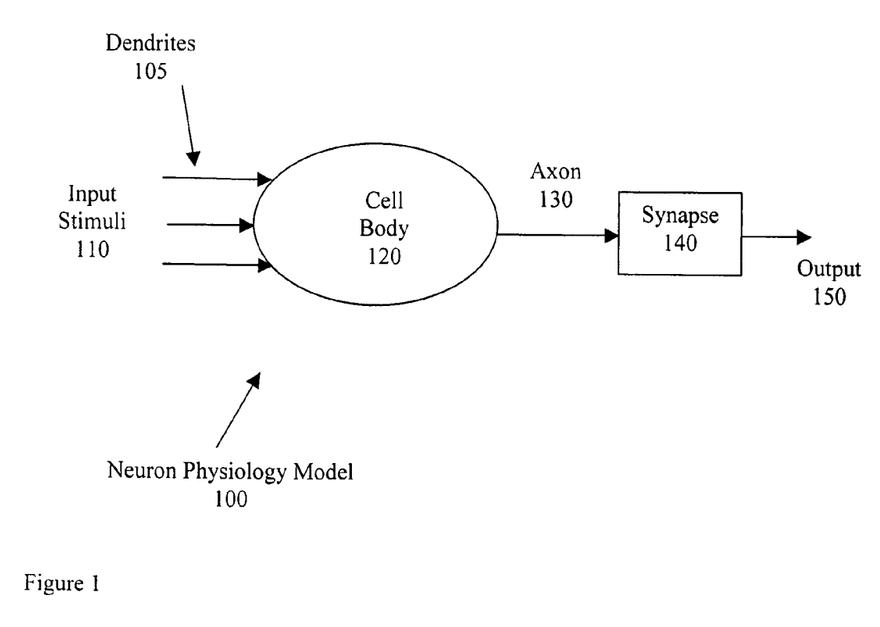
FIG. 1 is a schematic view of a neuron physiology model.

Neurons typically comprise axons feeding dendrites through synapses. The operation of such neurons is highly parallel, with each network element performing independently. A neuron is a simple element consisting of nodes and links which is part of a more complex network with each simple element performing as an independent processor. A simple neuron physiology model 100 is shown in FIG. 1 where, in neural physiology, dendrites 105 convey input stimuli 110 to a cell body 120, and an axon 130 conducts impulses away from the cell body 120. The neuron also has a distribution of ions both on its inside and on its outside. An action potential is a very rapid change in the distribution of these ions which result when the neuron is stimulated. Neurons typically adhere to the "All-or-None Law" in which action potentials occur maximally or not at all. The input stimuli 110 either activates the action potential or activation is not achieved and no action potential occurs. The synapse 140 of a neuron has a gap called the synaptic cleft which isolates the pre-synaptic components such as the dendrites 105, input stimuli 110, cell body 120 and axon 130 from the post-synaptic output 150.

Figure 2:
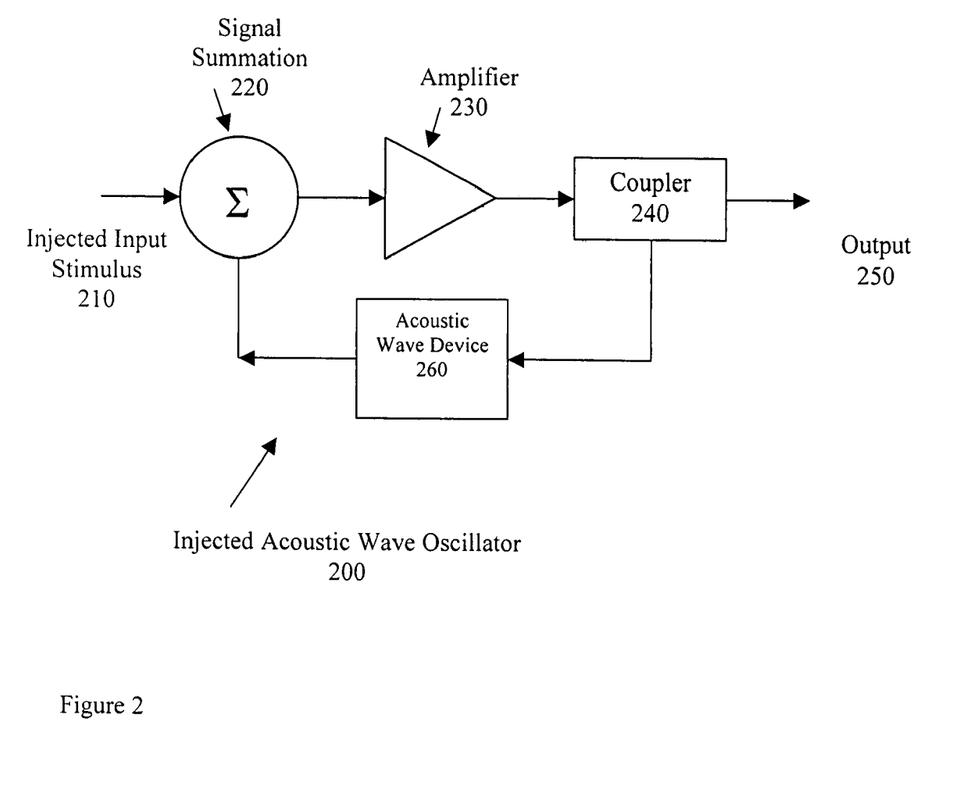
FIG. 2 is a similar view of an injected acoustic wave oscillator.

The use of injected acoustic wave devices to emulate neural networks was mentioned by Edmonson, (P. J. Edmonson et al, "SAW Injection Locked Oscillators: Dynamic Behaviour and Application to Neural Networks," IEEE Ultrasonics Symposium, 1993.), where the injected stimulus was an electrical signal a(t). FIG. 2 shows an injected acoustic wave oscillator 200 configured such that an injected input stimulus 210 acts as an input to a signal summation 220 from which the output is the input to an amplifier 230. The amplifier 230 is designed to provide sufficient gain to overcome any oscillator loop losses. The output of the amplifier 230 is the input to a coupler 240, which isolates the oscillator loop from an output 250. Another output of the coupler 250 is connected to an acoustic wave device 260 which provides a feedback element of the injected acoustic wave oscillator 200. The output of the acoustic wave device 260 acts as a second input to the signal summation 220 to complete the oscillator loop.

The injected acoustic wave oscillator 200 components comprising the signal summation 220, amplifier 230, coupler 240, acoustic wave device 260 and all oscillator loop connections and coupling factors are chosen such that the Barkhausen criteria is maintained and the output 250 signal follows equation (1), $$a(t)=A \sin(2\pi f_o t) \quad (1)$$

where A is the amplitude of the output 250, which is determined by the combination of the amplifier 230 and oscillator loop losses, and $f_o$ is the free-running frequency of the oscillator loop which is primarily determined by the frequency response of the acoustic wave device 260. The theory and method of injection locking an oscillator as outlined in, (P. J. Edmonson et al, "SAW Injection Locked Oscillators: Dynamic Behaviour and Application to Neural Networks," IEEE Ultrasonics Symposium, 1993.) and (P. J. Edmonson et al. "Injection Locking Techniques for a 1-GHz Digital Receiver Using Acoustic-Wave Devices," IEEE Transactions on Ultrasonics Ferroelectrics and Frequency Control, Vol. 39, No. 5, September 1992.) can be achieved by injecting a signal, $$b(t)=B \sin(2\pi f_i t) \quad (2)$$

where, B is the amplitude of the injected input stimulus 210 signal and $f_1$ is the frequency of the injected input stimulus 210 signal. Invariably, amplitude B of equation (2) is typically 50 db or more lower than amplitude A of equation (1), and the frequency stability of frequency $f_i$ of equation (2) is greater than that of frequency $f_o$ of equation (1).

As the injected input stimulus 210, b(t) of equation (2), is injected into the injected acoustic wave oscillator 200 and its amplitude B is sufficient, the injected acoustic wave output 250 switches to, $$a(t)=A \sin(2\pi f_i t) \quad (3)$$

where, $f_i$ is now the frequency of the injected input stimulus 210, b(t) of equation (2), the magnitude being equal to that of the amplitude A of equation (1). Once this transition has occurred and the output 250 has switched from equation (1) to equation (3), the system is stable, following the "All-or-None Law" and will not switch from equation (3) back to equation (1) until the injected input stimulus 210 is removed or the amplitude B of equation (2) is reduced sufficiently or conditions change within the injected acoustic wave oscillator 200 or a combination thereof.

Figure 3:
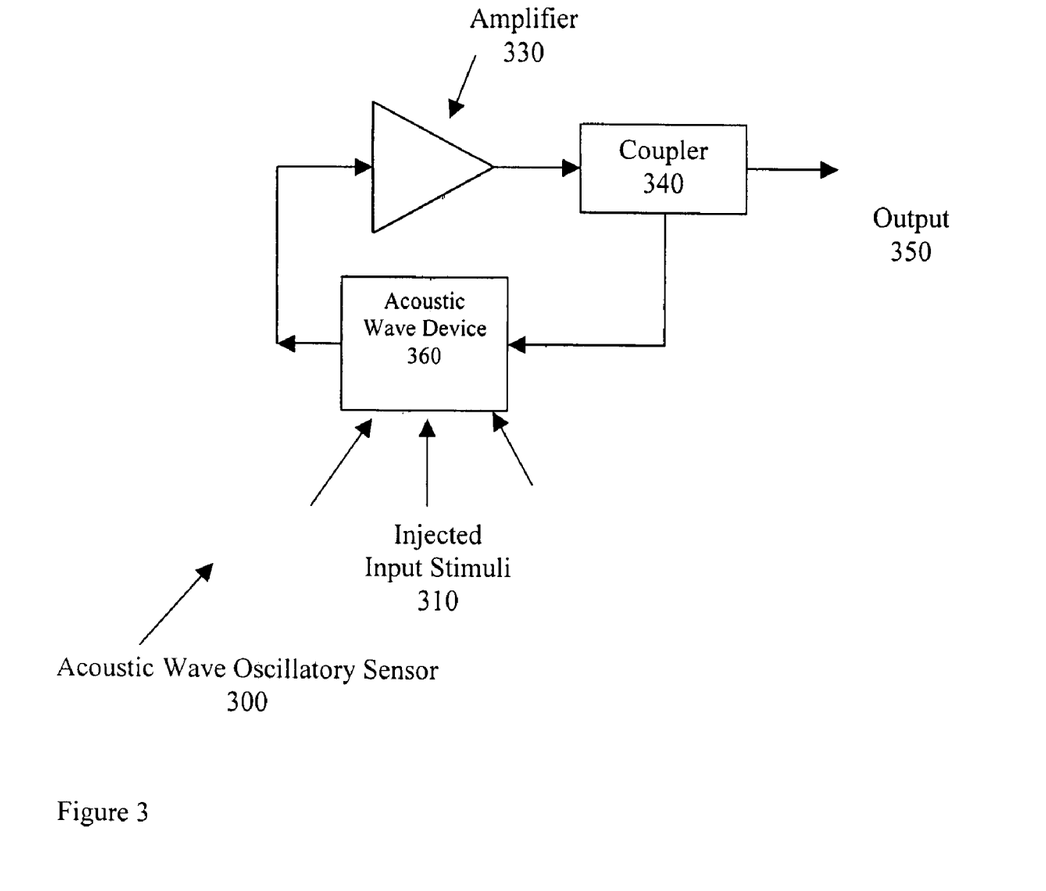
FIG. 3 is a similar view of an acoustic wave oscillatory sensor.

Similarly, another injection type oscillator can be derived as shown in FIG. 3. An acoustic wave oscillatory sensor 300 has injected input stimuli 310 which, when the acoustic wave oscillatory sensor 300 is properly configured, alters the frequency of the oscillator loop because the injected input stimuli 310 change the operating characteristics of the acoustic wave device 360. The main components which make up the acoustic wave oscillatory sensor 300 are amplifier 330, coupler 340, acoustic wave device 360 and all other oscillator loop connections and coupling factors which are chosen such that the Barkhausen criteria is maintained and the output (350) signal follows equation (1).

For this acoustic wave oscillatory sensor 300 application, the injected input stimuli 310 can be a physical, chemical or biological input which the sensor is designed to detect. The stimuli can include, but is not limited to, temperature, pressure, explosives, drugs and various biomarkers. As the injected input stimuli 310 interfaces with the acoustic wave device 360, the acoustic wave that propagates within the acoustic wave device 360 is subjected to a modification of its acoustic velocity. This change in velocity transcribes into a frequency change as shown in the modified Sauerbrey equation (4) mentioned in the publication by W. D. Hunt et al. ("Time-dependent signatures of acoustic wave biosensors," IEEE Proceedings, Vol. 91, no. 6, pp. 890-901, June 2003), $$\Delta f = -\frac{2f_u^2 h_f}{\sqrt{\rho_q \mu_q}}\left[\Delta \rho - \frac{\Delta \mu}{V_s^2}\right] \quad (4)$$

where $V_s$ is the acoustic velocity, $\rho$ is the density of the film, $h_f$ is the thickness of the film, $\mu_q$ and $\rho_q$ are the shear stiffness and density respectively of the quartz crystal, $\mu$ is the stiffness of the film, and $\Delta$ is the difference between perturbed and unperturbed (denoted by subscript u) quantities. The stiffness of the film, $\mu$ is affected by the conformational change of the recognition molecules.

The main concern with acoustic wave oscillatory sensor 300 is that it fails the "All-or-None Law" in that, as the injected input stimuli 310 interfaces with the acoustic wave device 360, the frequency of the acoustic wave oscillatory sensor 300 changes in a regressive fashion according to equation (4) but lacks any switching action within the acoustic wave oscillatory sensor 300.

Figure 4:
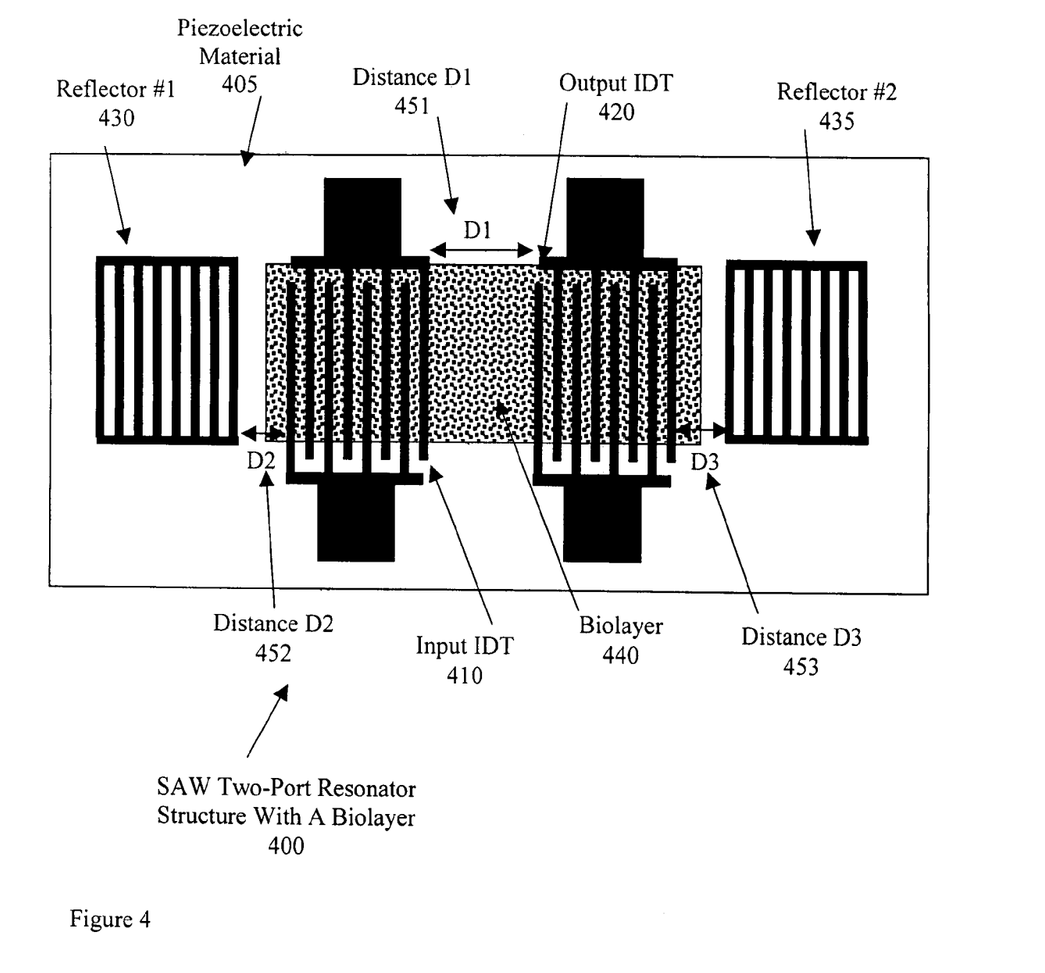
FIG. 4 is a diagrammatic view of a SAW two-port resonator structure with a biolayer.

The present invention enables the acoustic wave oscillatory sensor 300 to "switch" and adhere to the "All-or-None Law" by changing the construction of the acoustic wave device 360. An example of such a change in construction in accordance with the invention for a SAW two-port resonator structure with a biolayer 400 is shown in FIG. 4. A detailed description of SAW devices including two-port resonator structures and others can be found in the text by C. K. Campbell, Surface Acoustic Wave Devices for Mobile and Wireless Communications, Academic Press, 1998. In the SAW two-port resonator structure with a biolayer 400, a piezoelectric material 405 carries an input electrode assembly, namely an interdigital transducer (IDT) 410, and an output electrode assembly, namely an IDT 420, separated by a suitable distance D1 451.

When activated, an acoustic wave propagates bi-directionally from the input IDT 410 with one acoustic wave interfacing with the reflector #1 430 and reversing its propagation direction to propagate back towards the input IDT 410 and continuing on to the output IDT 420 and the reflector #2 435, where again the propagation direction is reversed and the propagation path continues on to the output IDT 420 and beyond. The other acoustic wave propagating from the input IDT 410 continues in a similar manner, initially towards the output IDT 420 and beyond. The result is that a resonant frequency is produced such that a single peak frequency response with a determined bandwidth results. The center frequency where this peak occurs is dependent on the geometries of the input IDT 410, the output IDT 420, reflector #1 430, reflector #2 435 and distances D1 451, D2 452 and D3 453. Distance D2, 452 is the separation between input IDT 410 and reflector #1 430, and distance D3 453 is the separation between output IDT 420 and reflector #2 435.

A biolayer 440 is then placed over areas of the piezoelectric material 405 in contact with various components of the structure, such as the input IDT 410 and output IDT 420. The purpose of the biolayer 440 is to permit specific binding of various analytes, which will then change the acoustic wave velocity and thereby produce a frequency change in accordance with equation (4). A further description of this method is presented by Hunt et al, "Clues From Digital Radio Regarding Biomolecular Recognition," IEEE transactions on Biomedical Circuits and Systems, vol. 1, no. 1, pp. 50-55, March 2007. When the geometries of both the input IDT 410 and output IDT 420 are identical, and reflector #1 430, reflector #2 435 and distances D1 451, D2 452 and D3 453 are suitably chosen, then a frequency response centered at frequency ($f_o$) is generated. As the binding of the chosen analytes occurs within the biolayer 440, the frequency response centered at ($f_o$) will shift down in frequency in accordance with equation (4).

Figure 5:
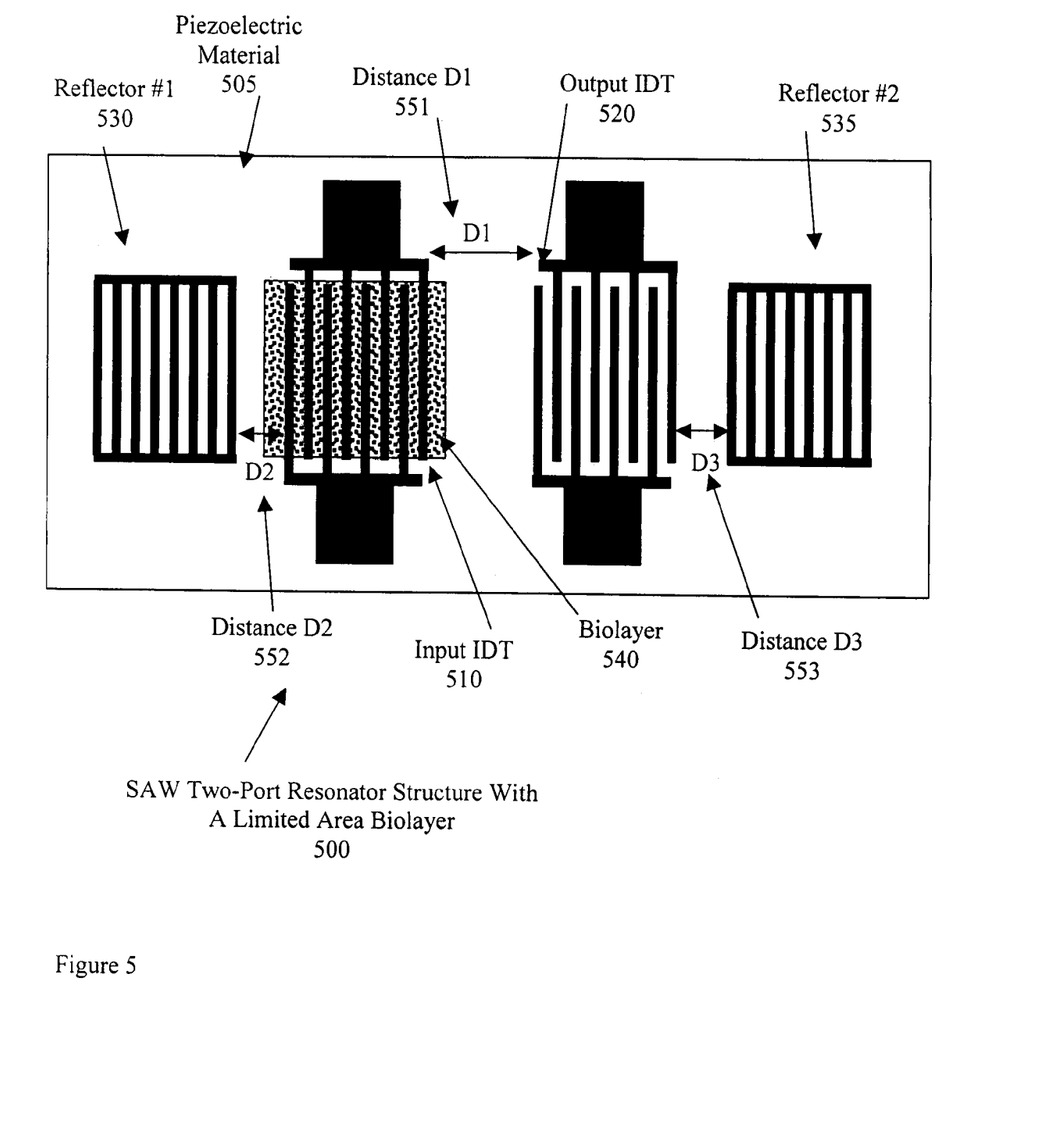
FIG. 5 is a similar view of a SAW two-port resonator structure with a limited area biolayer.

A SAW two-port resonator structure with a limited area biolayer 500 is shown in FIG. 5. The biolayer 540 is placed only in proximity to the input IDT 510. All other components, such as the piezoelectric material 505, output IDT 520, reflector #1 530, reflector #2 535 and distances D1 551, D2 552 and D3 553 remain and operate similarly as described previously for the SAW two-port resonator structure with a biolayer 400 in FIG. 4. When the center frequency of the output IDT 520 is purposely designed to a specific frequency, the input IDT 510 is purposely designed for a center frequency above that of the output IDT 520 and reflector #1 530, reflector #2 535 and distances D1 551, D2 552 and D3 553 are suitably chosen, then a frequency response depicting two resonant peaks results.

Figure 6:
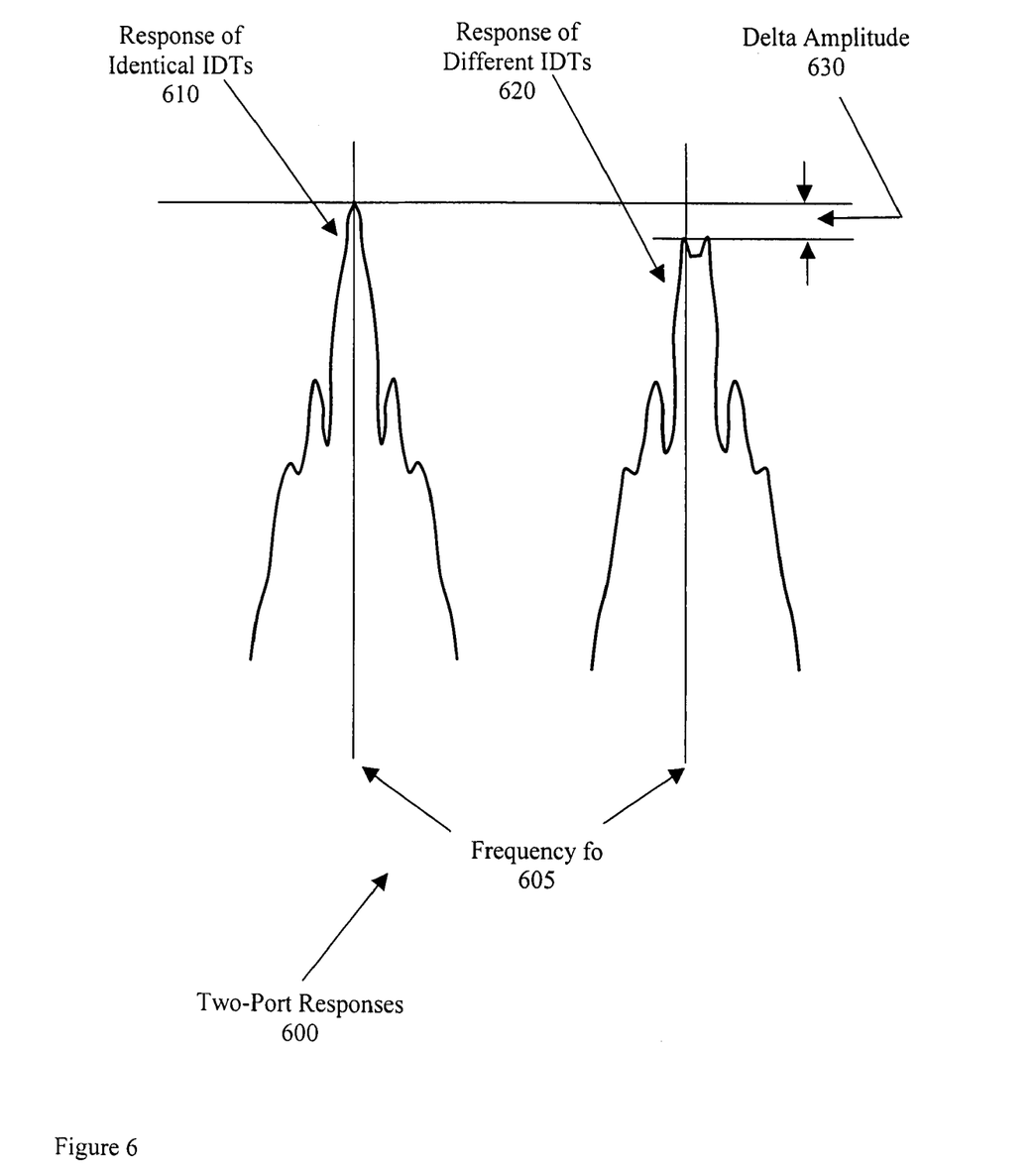
FIG. 6 is a graph showing two-port responses.

A comparison of the two-port responses 600 is shown in FIG. 6. The response 610 of identical input and output IDTs, as shown in FIG. 4, is a typical single peak at a center frequency $f_0$ 605. The response 620 of different input and output IDTs, as shown in FIG. 5, has two peaks, with one being designed for frequency $f_o$ 605, as explained previously for the output IDT 520, and the other being designed for a frequency ($f_o+\Delta f$) as explained previously for the input IDT 510. Since the configuration of different input and output IDTs, such as shown in FIG. 5, is not at a single resonance, the amplitude of the response 620 of different input and output IDTs is of lower amplitude that that of the response 610 of identical input and output IDTs. The difference in relative amplitude can be illustrated by delta amplitude 630.

Two major events take place as the biolayer 540 begins to bind with selected substances. The operational frequency of the input IDT 510 reduces from ($f_0+\Delta f$) to about $f_o$ according to equation (4), and the delta amplitude 630 begins to decrease to zero. This also has the effect of changing the response 620 of different input and output IDTs to that of the response of identical input and output IDTs. The SAW two-port resonator structure with a limited area biolayer 500 is then incorporated in the configuration of the acoustic wave oscillatory sensor 300 shown in FIG. 3. The gain of the amplifier 330 is chosen so that the oscillator loop does not initially meet the Barkhausen criteria due to the increased insertion loss illustrated by the delta amplitude 630. As the injected input stimuli 310 interfaces with the acoustic wave device 360 containing the SAW two-port resonator structure with a limited area biolayer 500, the acoustic wave associated with the input IDT 510 is subjected to a modification of its acoustic velocity in accordance with equation (4) if and only if the biolayer 540 is compatible with the injected input stimuli 310. The biolayer 540 will not react with the injected input stimuli 310 if the two components are not compatible, and no change in the acoustic velocity will take place. If the injected input stimuli 310 binds with a threshold amount of compatible substances onto the biolayer 540, there will be sufficient frequency shift to alter the response of different input and output IDTs 620 to that of the response of identical input and output IDTs 610, and reduce the delta amplitude 630 resulting in the Barkhausen criteria for gain to be met so the oscillator will begin to oscillate and continue to oscillate until circuit conditions change. Therefore the acoustic wave oscillatory sensor 300 will switch from an OFF state to an ON state, producing an output 350 as a function of the injected input stimuli 310.

Figure 7:
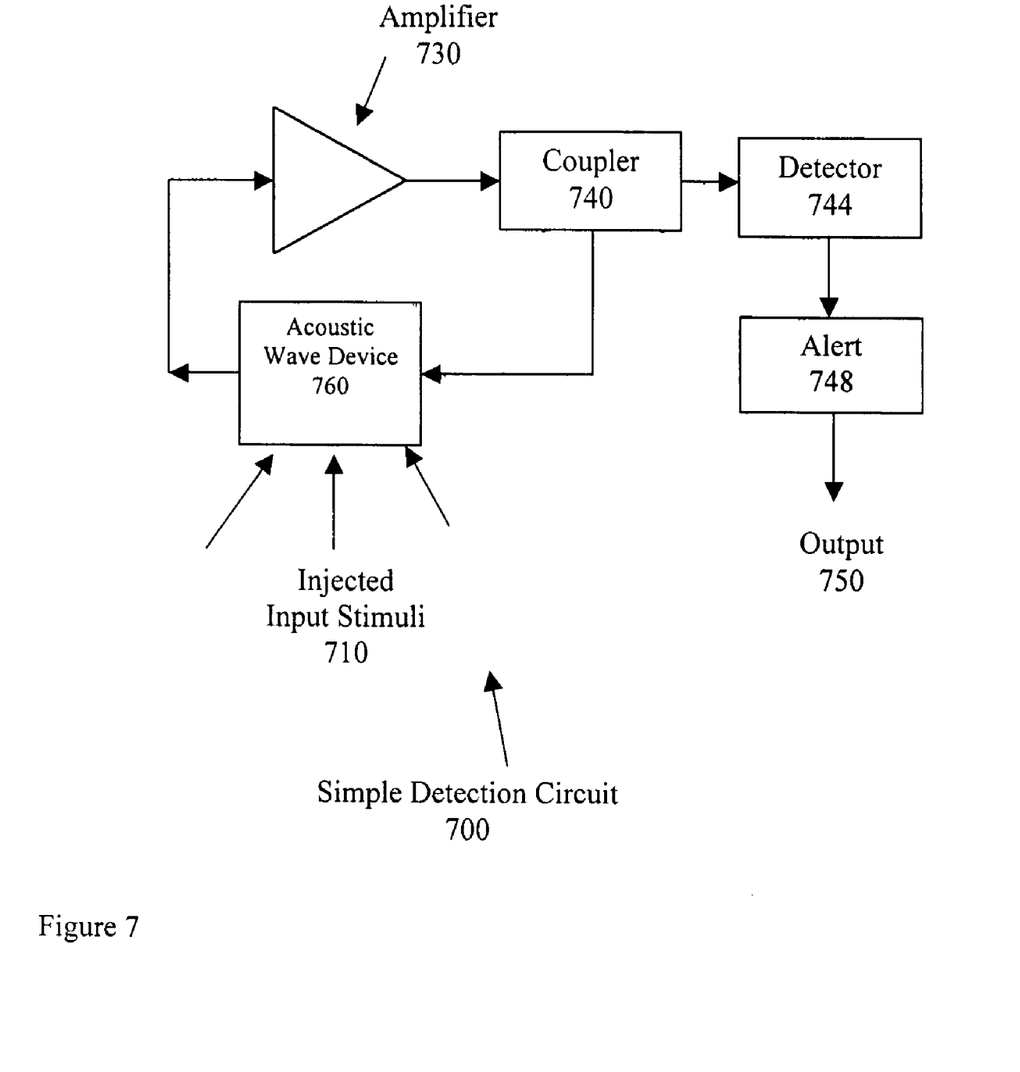
FIG. 7 is a schematic view of a simple detection circuit.

A simple detection circuit 700 is shown in FIG. 7, in which the only active electrical components are the amplifier 730, the detector 744 and the alert 748. No data sampling or data conversion, such as an analog-to-digital converter (ADC), filtering or microprocessor or other ancillary circuitry is required. The detector 744 may be a simple diode detector with a Schmidt trigger and a latch or other similar type of circuit. The alert 748 may be a simple light emitting device, an audible emitting device or other suitable alerting device such as a relay or wireless type of circuit. The detection circuit 700 now meets the "All-or-None Law" of a neuron because the output 750 remains in the OFF state until the detection circuit 700 switches due to a threshold amount of compatible injected input stimuli 710 reacting with a selected biolayer similar to that of a SAW two-port resonator structure with a limited area biolayer 500 when substituted for the acoustic wave device 760.

A home mold detector using the detection circuits 700 may have a compatible mold specific biolayer 540 attached to the acoustic wave device 760 in a manner similar to the SAW two-port resonator structure with a limited area biolayer 500. A user would remove the detection circuit 700 from a hermetically sealed bag or equivalent, turn on the detection circuit 700 and then place it over an output of the home ventilation system or other suitable area to be tested. After a set amount of time determined by the amount of mold present within the test area, the detection circuit 700 will activate the alert 748 to produce a suitable output 750 if sufficient mold is present. If there is insufficient mold present within the test area, then the alert 748 will not activate the output 750.

Figure 8:
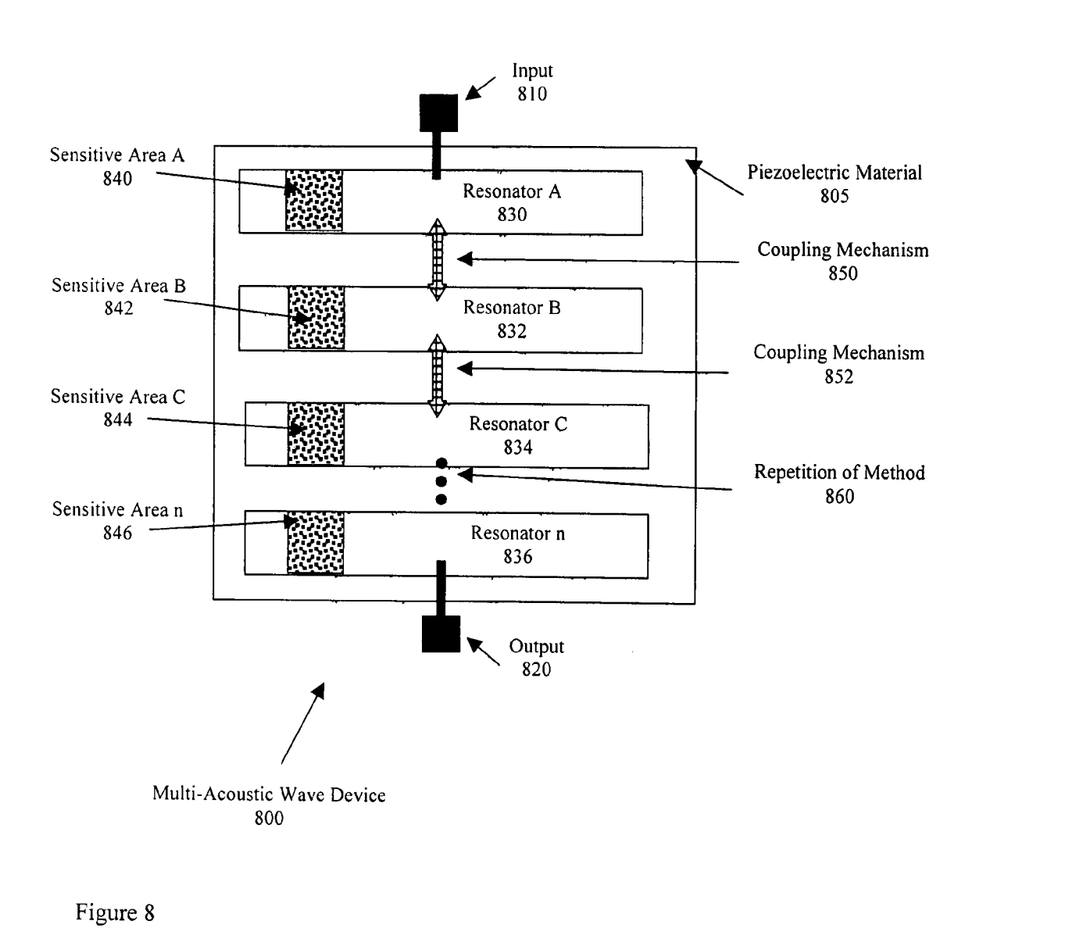
FIG. 8 is a similar view of a multi-acoustic wave device.

The previous example describes an use of a simple detection circuit 700 based on a SAW two-port resonator structure with a limited area biolayer 500. It was assumed however that only one stimulus needed to be detected, and an acoustic wave device was used such in such a manner that two frequency peaks could be achieved by choosing two different operating frequencies for the input and output IDTs. FIG. 8 shows a multi-acoustic wave device 800 which serially connects several acoustic wave devices, each having the capability of its own sensitive area. The number of acoustic wave devices within the multi-acoustic wave device 800 is dependent upon the intended use. This sensitive area is constructed so that a physical, chemical or biological stimulus of the sensitive area affects the acoustic wave parameters, and may for example be a biolayer. The multi-acoustic wave device 800 would be connected as previously described in the detection circuit 700 of FIG. 7 where it would replace the acoustic wave device 760. The input 810 and output 820 would be suitably connected to respective components in the detection circuit 700. The multi-acoustic wave device 800 would be placed on a suitable piezoelectric material 805. The piezoelectric material 805 would be chosen from materials which would support bulk acoustic waves, surface acoustic waves, thin film bulk acoustic waves (FBAR) or other modes known to those skilled in the art. Each of the several resonators, resonator A 830, resonator B 832, and resonator C 843 continuing to resonator n 836 may be a one-port acoustic wave resonator or a two-port acoustic wave resonator or have other acoustic wave configurations utilizing three or more IDTs as described by Edmonson et al, "Radiation Conductance and Grating Reflectivity Weighting Parameters for Dual Mode Leaky-SAW Resonator Filter Design," IEEE Ultrasonics Symposium, 1994.

Each of the several resonators, resonator A 830, resonator B 832, and resonator C 843 continuing to resonator n 836 will have a sensitive area placed on them such that a physical, chemical or biological stimulus of the sensitive area affects the acoustic wave parameters, and may be a biolayer. Such resonators may be directly electrically connected or acoustically coupled. Simple electrical connections may include conductive paste, conductive wires, conductive tracks on a printed circuit board or conductive thin film material or other commonly used techniques. Acoustic coupling may include, but is not limited to, the mechanism described by C. K. Campbell, P. M. Smith and P. J. Edmonson, "Aspects of modelling the frequency response of a two-port waveguide-coupled SAW resonator-filter," IEEE Transactions on Ultrasonics, Ferroelectrics and Frequency Control, vol. 39, no. 6, pp. 768-773, November 1992 or other suitable acoustic means. The electrical signal which is conveyed from the input 810 to the first resonator A 830 is then coupled via a coupling mechanism 850 to resonator B 832 and then if required either onto the output 820 or via a coupling mechanism 852 to resonator C 834. If required, this is continued with repetition of method 860 to resonator n 836. The sensitive area A 840 is suitably located on resonator A 830 such that, as the sensitive area A 840 reacts to a stimulus, the resulting resonant frequency peak of the resonator A 830 structure will shift in accordance with equation (4). Similarly, sensitive area B 842 is suitably located on resonator B 832, sensitive area C 844 is suitably located on resonator C 834 and so on to sensitive area n 846 suitably located on resonator n 836 such that, as the chosen stimuli reacts with sensitive area B 842, sensitive area C 844 and continuing to sensitive area n 846 the resulting resonant frequency peaks of resonator B 832, and resonator C 834 continuing to resonator n 836 structures respectively, will shift in accordance with equation (4).

For some uses of this invention, the sensitive area placed on the resonator, such as a biolayer, will not be activated and hence will not react with physical, chemical or biological stimuli resulting in a zero shift of the resonant frequency peak. This configuration would be useful for one-port resonator uses where, for example, resonator A 830 is fixed at frequency $f_o$ and its sensitive area A 840 is not active. The remaining resonators would be constructed such that their resonant frequency peaks are at $f_1$ where $f_1=(f_o+xf)$ and their respective sensitive areas were activated so that, as stimuli take effect $\Delta f$ will be reduced in accordance with equation (4) and all resonators will be synchronized at or near the frequency $f_o$.

Figure 9:
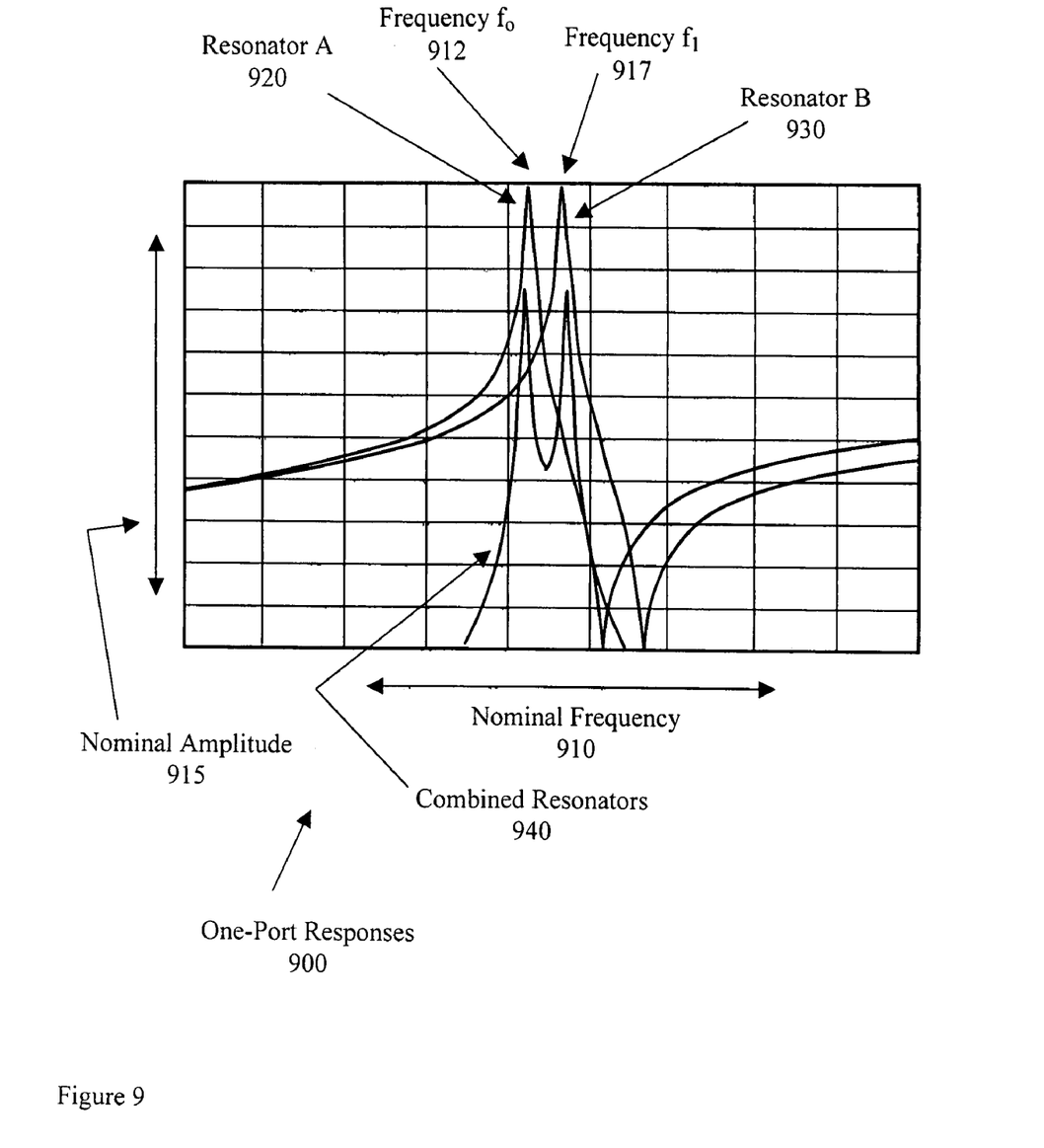
FIG. 9 is a graph showing one-port responses.

An illustration of one-port responses 900 is shown in FIG. 9, with the x-axis representing the nominal frequency 910 and the y-axis representing the nominal amplitude 915. Resonator A 920 is chosen to be fixed at frequency $f_0$ 912, and resonator B 930 is chosen to be at frequency $f_1$ 917 where $f_1=(f_o+\Delta f)$. The combined resonators 940, as previously configured in FIG. 8, produce a response which is lower in nominal amplitude. As the selected area of resonator B 930 begins to react with the input stimulus, the frequency $f_1$ 917 of resonator B 930 reduces from $(f_o+\Delta f)$ to about $f_0$ in accordance with equation (4) and the combined response of resonators (940) changes to that of approximately resonator A 920, the over all insertion loss of the combined resonators 940 is reduced and the Barkhausen criteria for gain would be met to produce an oscillatory output. This process when including "n" different resonators as previously shown in FIG. 8 would in effect produce an (n−1) input AND gate function if one resonator did not have its sensitive area activated or an (n) input AND gate function if all resonators had an active sensitive area. This AND gate function would only activate if and only if all of the stimuli were present and of sufficient magnitude such that the resonators will align in close proximity to the same frequency $f_o$ 912 and that the overall normalized amplitude of all the resonators when combined with an amplifier and other oscillator circuitry meet the threshold limit of the Barkhausen criteria for gain to produce an oscillatory output.

Other embodiments and advantages of the invention will now be readily apparent to a person skilled in the art from the foregoing description, scope of the invention being defined in the appended claims.

The invention claimed is:

1. A sensing system including a detector and an oscillating circuit comprising a coupling device, an amplifier, and a plurality of resonators, wherein:
   each resonator comprises:
      (i) a body of piezoelectric material;
      (ii) an input electrode assembly mounted on the body of piezoelectric material whereby the input electrode assembly when activated produces an acoustic wave across the body of piezoelectric material; and
      (iii) an output electrode assembly mounted on the body of piezoelectric material and being in contact with a sensitive area that is sensitive to a supplied stimulus so that the acoustic velocity of the acoustic wave across the sensitive area is modified when a supplied stimulus binds to the sensitive area in sufficient quantity, whereby the output electrode assembly receives the acoustic wave after the acoustic wave has passed across the sensitive area; and
   wherein for each resonator, when the input electrode assembly is activated, the input electrode assembly and the output electrode assembly cooperate to produce a frequency response representative of one of presence or absence of a sufficient quantity of the stimulus;
   wherein the resonators are coupled in series from 1 to n;
   and wherein:
   the $n^{th}$ resonator has an output connected to an amplifier input of the amplifier;
   the amplifier has an amplifier output connected to a coupling device input of the coupling device;
   the coupling device has a first coupling device output connected to an input of the first resonator;
   the coupling device has a second coupling device output connected to the detector; and
   the amplifier has a gain that is insufficient to cause the oscillator circuit to meet Barkhausen criteria when at least one of the n resonators produces a frequency response representative of absence of a sufficient quantity of its respective stimulus and that is sufficient to cause the oscillator circuit to meet Barkhausen criteria when all of the n resonators produce a frequency response representative of presence of a sufficient quantity of their respective stimulus, so that the detector emits a detection signal only when all of the n resonators produce a frequency response representative of presence of a sufficient quantity of their respective stimulus.

2. The sensing system of claim 1, wherein the n resonators are electrically connected in series.

3. The sensing system of claim 2, wherein each wave produced by each respective first electrode assembly is a surface acoustic wave.

4. The sensing system of claim 1, wherein the n resonators are acoustically coupled in series.

5. The sensing system of claim 4, wherein each wave produced by each respective first electrode assembly is a surface acoustic wave.

6. The sensing system of claim 1, wherein each sensitive area is sensitive to a different stimulus.

7. The sensing system of claim 6, wherein each wave produced by each respective first electrode assembly is a surface acoustic wave.

8. The sensing system of claim 1, wherein at least one sensitive area comprises molecular recognition elements.

9. The sensing system of claim 8, wherein each wave produced by each respective first electrode assembly is a surface acoustic wave.

10. The sensing system of claim 1, wherein at least one sensitive area comprises antibodies.

11. The sensing system of claim 10, wherein each wave produced by each respective first electrode assembly is a surface acoustic wave.

12. The sensing system of claim 1, wherein the resonators comprise respective first and second electrode assemblies mounted on a common body of piezoelectric material.

13. The sensing system of claim 12, wherein each wave produced by each respective first electrode assembly is a surface acoustic wave.

14. The sensing system of claim 1, wherein each resonator comprises first and second electrode assemblies mounted on a separate body of piezoelectric material.

15. The sensing system of claim 14, wherein each wave produced by each respective first electrode assembly is a surface acoustic wave.

16. The sensing system of claim 1, further comprising a reference resonator whose sensitive area is inactivated connected as a first resonator in the series.

17. The sensing system of claim 16, wherein each wave produced by each respective first electrode assembly is a surface acoustic wave.

18. The sensing system of claim 1, wherein each wave produced by each respective first electrode assembly is a surface acoustic wave.

* * * * *